United States Patent
Bowman et al.

(10) Patent No.: US 7,867,192 B2
(45) Date of Patent: Jan. 11, 2011

(54) AMBULATORY INFUSION DEVICES AND METHODS WITH BLOCKAGE DETECTION

(75) Inventors: Sam W. Bowman, Valencia, CA (US); Brian Michael Shelton, Pasadena, CA (US); Scott R. Gibson, Granada Hills, CA (US); Lawrence Eric Ong, Beverly Hills, CA (US); John Paul D'Brot, Santa Clarita, CA (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 131 days.

(21) Appl. No.: 12/040,468

(22) Filed: Feb. 29, 2008

(65) Prior Publication Data

US 2009/0221957 A1    Sep. 3, 2009

(51) Int. Cl.
    *A61M 31/00*    (2006.01)
(52) U.S. Cl. .................. 604/67; 604/28; 604/500
(58) Field of Classification Search ............. 604/67, 604/31, 505, 28, 500
    See application file for complete search history.

(56) References Cited

U.S. PATENT DOCUMENTS

| | | | |
|---|---|---|---|
| 3,926,056 A | 12/1975 | Brown | |
| 4,013,074 A | 3/1977 | Siposs | |
| 4,530,696 A * | 7/1985 | Bisera et al. ............... 604/253 | |
| 4,557,726 A | 12/1985 | Reinicke | |
| 4,636,150 A * | 1/1987 | Falk et al. ................. 417/417 | |
| 4,690,673 A | 9/1987 | Bloomquist | |
| 4,714,462 A | 12/1987 | DiDomenico | |
| 4,718,893 A | 1/1988 | Dorman et al. | |
| 5,006,997 A | 4/1991 | Reich | |
| 5,190,522 A | 3/1993 | Wojcicki et al. | |
| 5,356,378 A * | 10/1994 | Doan ............................ 604/65 | |
| 5,695,473 A | 12/1997 | Olsen | |
| 5,785,681 A | 7/1998 | Indravudh | |
| 5,935,106 A | 8/1999 | Olsen | |
| 5,989,222 A | 11/1999 | Cole et al. | |
| 6,231,560 B1 | 5/2001 | Bui et al. | |
| 6,354,999 B1 | 3/2002 | Dgany et al. | |
| 6,423,029 B1 | 7/2002 | Elsberry | |
| 6,595,756 B2 | 7/2003 | Gray et al. | |
| 6,620,151 B2 | 9/2003 | Blischak et al. | |
| 7,022,116 B2 | 4/2006 | Morris | |
| 7,054,782 B2 | 5/2006 | Hartlaub | |
| 2004/0260229 A1 | 12/2004 | Meir | |
| 2005/0038360 A1 | 2/2005 | Shertukde et al. | |
| 2005/0075624 A1* | 4/2005 | Miesel ........................ 604/505 | |

(Continued)

FOREIGN PATENT DOCUMENTS

DE    19642234 C1    4/1998

(Continued)

OTHER PUBLICATIONS

PCT Int. Search Report and Written Opinion dated Apr. 9, 2009 for PCT App. No. PCT/US09/033352.

*Primary Examiner*—Nicholas D Lucchesi
*Assistant Examiner*—Leah Stohr
(74) *Attorney, Agent, or Firm*—Henricks, Slavin & Holmes LLP

(57) ABSTRACT

Infusion devices with blockage detection capability and methods of monitoring infusion devices.

23 Claims, 4 Drawing Sheets

| U.S. PATENT DOCUMENTS | | |
|---|---|---|
| 2005/0090799 A1 | 4/2005 | Morris |
| 2008/0021395 A1 | 1/2008 | Yodfat et al. |

| FOREIGN PATENT DOCUMENTS | | |
|---|---|---|
| WO | WO-96/27398 A1 | 9/1996 |
| WO | WO-99/55225 A1 | 11/1999 |
| WO | WO-2006/127508 A2 | 11/2006 |

* cited by examiner

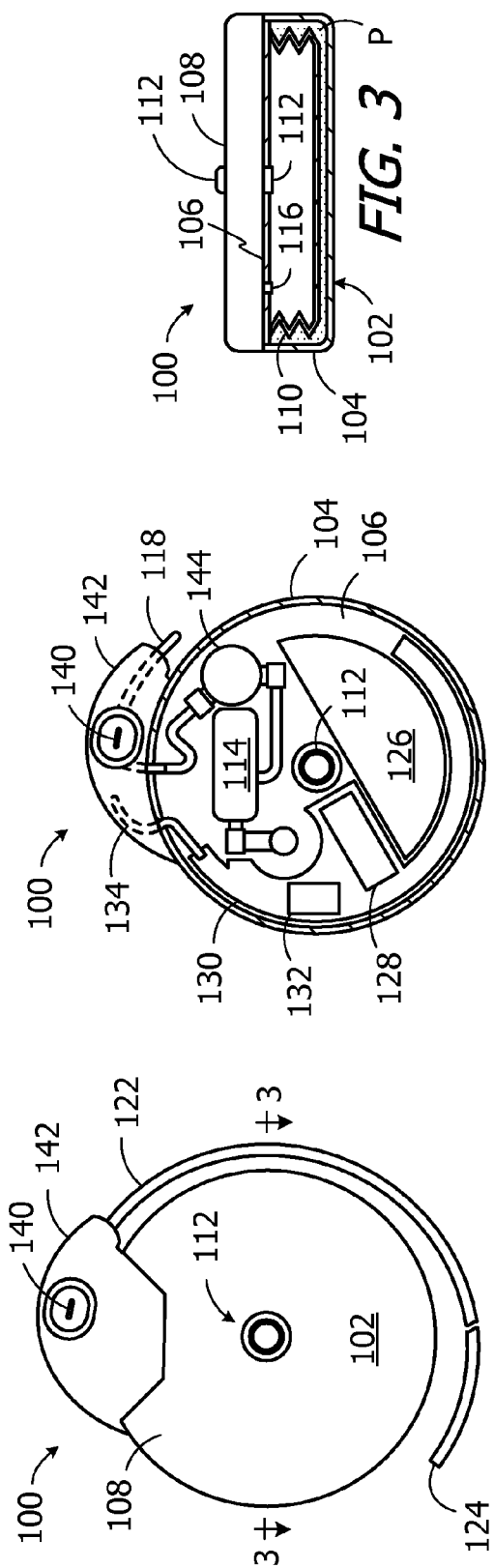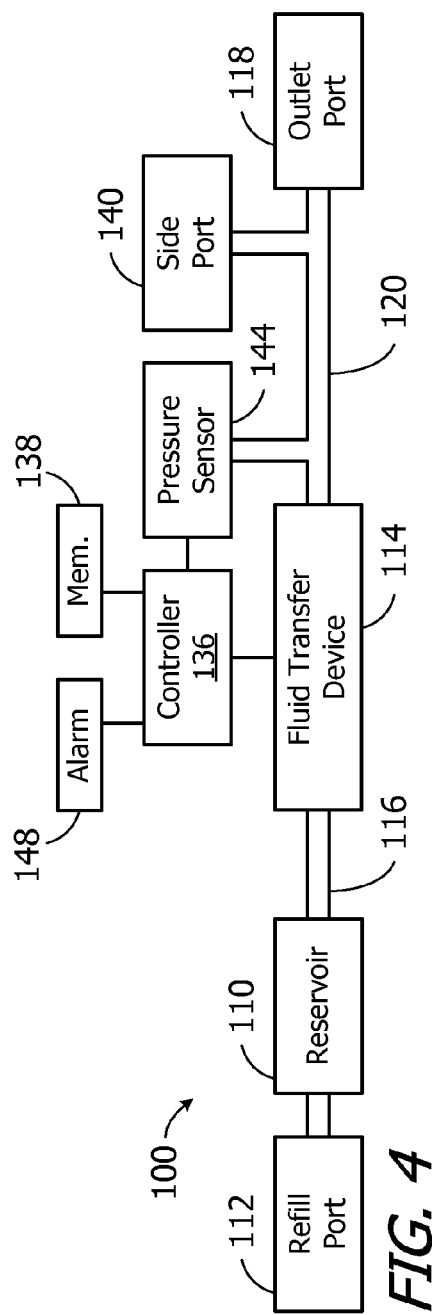

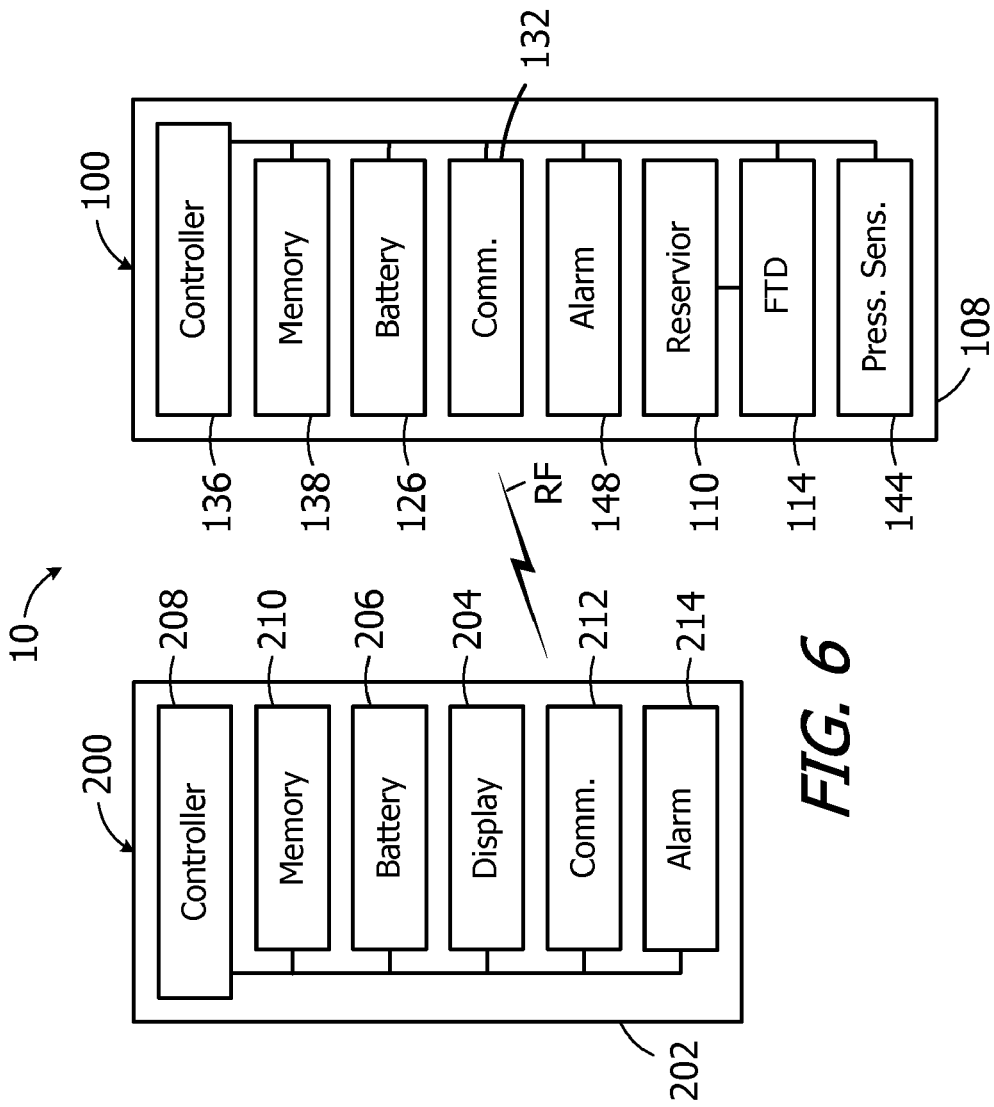
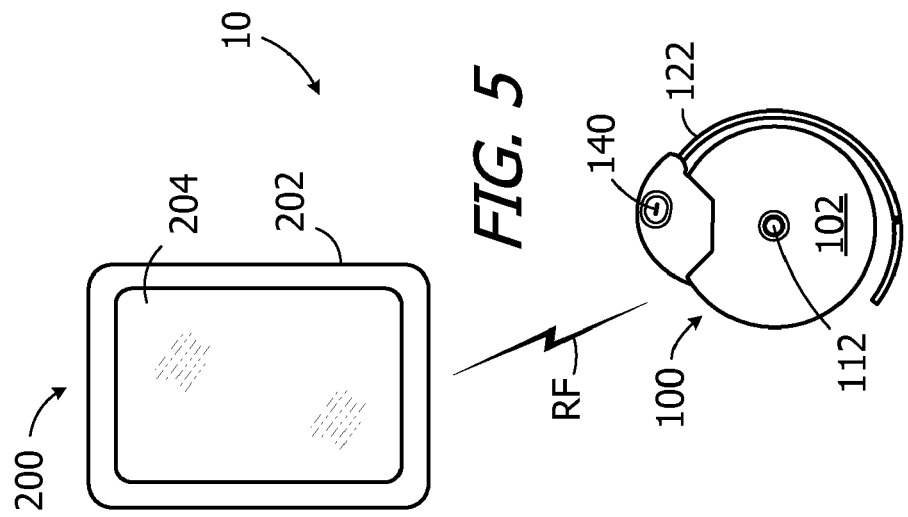

AMBULATORY INFUSION DEVICES AND METHODS WITH BLOCKAGE DETECTION

BACKGROUND OF THE INVENTIONS

1. Field of Inventions

The present inventions relate generally to ambulatory infusion devices.

2. Description of the Related Art

Ambulatory infusion devices, such as implantable infusion devices and externally carried infusion devices, have been used to provide a patient with a medication or other substance (collectively "infusible substance") and frequently include a reservoir and a pump. The reservoir is used to store the infusible substance and, in some instances, implantable infusion devices are provided with a fill port that allows the reservoir to be transcutaneously filled (and/or re-filled) with a hypodermic needle. The reservoir is coupled to the pump, which is in turn connected to an outlet port. A catheter, which has an at least one outlet at the target body region, may be connected to the outlet port. As such, infusible the reservoir may be transferred from the reservoir to the target body region by way of the pump and catheter.

There are a number of blockage-related issues that can prevent an ambulatory infusion device from functioning properly. Catheters, for example, may become partially or completely blocked (collectively "blocked") by the formation of tissue at the catheter outlet. Catheters may also develop kinks that can partially or completely block fluid flow. Partial blockages can prevent the patient from receiving the intended dosage of the infusible substance, while complete blockages will prevent any of the infusible substance from reaching the patient.

The present inventors have determined that conventional methods of detecting blockages are susceptible to improvement. For example, some conventional methods of detecting blockages rely on catheter pressure measurements and, more specifically, on measured increases in catheter pressure. The present inventors have determined that conventional pressure-based methods of detecting blockages can be inaccurate in that they may determine that a blockage is present when in fact no blockage is present (referred to herein as "a false blockage determination") as a result of changes in environmental pressure.

SUMMARY OF THE INVENTIONS

The present apparatus and methods analyze pressure measurements in the context of other factors. Such apparatus and methods substantially reduce the likelihood that false blockage determinations will occur as a result of changes in environmental pressure.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIG. 1 is a plan view of an implantable infusion device in accordance with one embodiment of a present invention.

FIG. 2 is a plan view of the implantable infusion device illustrated in FIG. 1 with the cover removed.

FIG. 3 is a partial section view taken along line 3-3 in FIG. 1.

FIG. 4 is a block diagram of the implantable infusion device illustrated in FIGS. 1-3.

FIG. 5 is a plan view of an implantable infusion device system in accordance with one embodiment of a present invention.

FIG. 6 is a block diagram of the implantable infusion device system illustrated in FIG. 5.

DETAILED DESCRIPTION OF THE EXEMPLARY EMBODIMENTS

Figure 7:
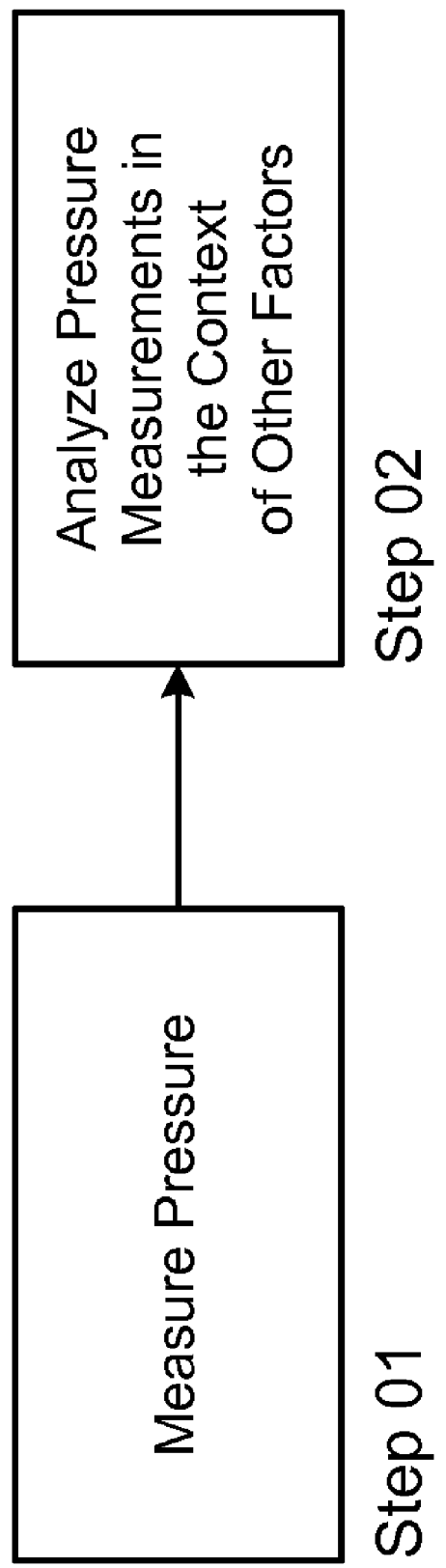
FIG. 7 is a flow chart in accordance with one embodiment of a present invention.

The following is a detailed description of the best presently known modes of carrying out the inventions. This description is not to be taken in a limiting sense, but is made merely for the purpose of illustrating the general principles of the inventions. The present inventions are also not limited to the exemplary implantable infusion device described herein and, instead, are applicable to other implantable or otherwise ambulatory infusion devices that currently exist or are yet to be developed.

One example of an implantable infusion device in accordance with a present invention is generally represented by reference numeral 100 in FIGS. 1-4. As used herein, an "implantable infusion device" is a device that includes a reservoir and an outlet, and is sized, shaped and otherwise constructed (e.g. sealed) such that both the reservoir and outlet can be simultaneously carried within the patient's body. The exemplary infusion device 100 includes a housing 102 (e.g. a titanium housing) with a bottom portion 104, an internal wall 106, and a cover 108. An infusible substance (e.g. medication) may be stored in a reservoir 110 that is located within the housing bottom portion 104. The reservoir 110 may be replenished by way of a refill port 112 that extends from the reservoir, through the internal wall 106, to the cover 108. A hypodermic needle (not shown), which is configured to be pushed through the refill port 112, may be used to replenish the reservoir 110.

A wide variety of reservoirs may be employed. In the illustrated embodiment, the reservoir 110 is in the form of a titanium bellows that is positioned within a sealed volume defined by the housing bottom portion 104 and internal wall 106. The remainder of the sealed volume is occupied by propellant P, which may be used to exert negative pressure on the reservoir 110. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure that is always negative with respect to the ambient pressure.

The exemplary ambulatory infusion device 100 illustrated in FIGS. 1-4 also includes a fluid transfer device 114. The inlet of a fluid transfer device 114 is coupled to the interior of the reservoir 110 by a passageway 116, while the outlet of the fluid transfer device is coupled to an outlet port 118 by a passageway 120. Operation of the fluid transfer device 114 causes infusible substance to move from the reservoir 110 to the outlet port 118. A catheter 122 may be connected to the outlet port 118 so that the infusible substance passing through the outlet port will be delivered to a target body region in spaced relation to the infusion device 100 by way of the outlet 124 at the end of the catheter.

A wide variety of fluid transfer devices may be employed. In the illustrated embodiment, the fluid transfer device 114 is in the form of an electromagnet pump. The present inventions are not, however, limited to electromagnet pumps and may include other types of fluid transfer devices. Such devices include, but are not limited to, other electromagnetic pumps, solenoid pumps, piezo pumps, and any other mechanical or electromechanical pulsatile pump. In the exemplary context of implantable drug delivery devices, and although the volume/stroke magnitude may be increased in certain situations, the fluid transfer devices will typically deliver about 1 microliter/stroke, but may be more or less (e.g. about 0.25 microliter/stroke or less) depending on the particular fluid transfer device employed. Additionally, although the exemplary fluid transfer device 114 is provided with internal valves (e.g. a main check valve and a bypass valve), valves may also be provided as separate structural elements that are positioned upstream of and/or downstream from the associated fluid transfer device.

Energy for the fluid transfer device 114, as well for other aspects of the exemplary infusion device 100, is provided by the battery 126 illustrated in FIG. 2. In the specific case of the fluid transfer device 114, the battery 126 is used to charge one or more capacitors 128, and is not directly connected to the fluid transfer device itself. The capacitor(s) 128 are connected to an electromagnet coil in the fluid transfer device 114, and disconnected from the battery 126, when the electromagnet coil is being energized, and are disconnected from the electromagnet coil and connected to the battery when the capacitor(s) are being recharged and/or when the fluid transfer device is at rest. The capacitor(s) 128 are carried on a board 130. A communication device 132, which is connected to an antenna 134, is carried on the same side of the board 130 as the capacitor(s) 128. The exemplary communication device 132 is an RF communication device. Other suitable communication devices include, but are not limited to, oscillating magnetic field communication devices, static magnetic field communication devices, optical communication devices, ultrasound communication devices and direct electrical communication devices.

A controller 136 (FIG. 4), such as a microprocessor, microcontroller or other control circuitry, is carried on the other side of the board 130. The controller controls the operations of the infusion device 100 in accordance with instructions stored in memory 138 and/or provided by an external device (e.g. the remote control 200 described below) by way of the communication device 132. For example, the controller 136 may be used to control the fluid transfer device 114 to supply fluid to the patient in accordance with, for example, a stored basal delivery schedule or a bolus delivery request. The controller 136 may also be used to monitor sensed pressure and perform the analytical functions described below.

Referring to FIGS. 1, 2 and 4, the exemplary infusion device 100 is also provided with a side port 140 that is connected to the passageway 120 between the outlet of the fluid transfer device 114 and the outlet port 118. The side port 140 facilitates access to an implanted catheter 122, typically by way of a hypodermic needle. For example, the side port 140 allows clinicians to push fluid into the catheter 122 and/or draw fluid from the catheter for purposes such as checking catheter patency, sampling CSF, injecting contrast dye into the patient and/or catheter, removing medication from the catheter prior to dye injection, injecting additional medication into the region at the catheter outlet 124, and/or removing pharmaceuticals or other fluids that are causing an allergic or otherwise undesirable biologic reaction.

The outlet port 118, a portion of the passageway 120, the antenna 134 and the side port 140 are carried by a header assembly 142. The header assembly 142 is a molded, plastic structure that is secured to the housing 102. The housing 102 includes a small aperture through which portions of the passageway 120 are connected to one another, and a small aperture through which the antenna 134 is connected to the board 130.

The exemplary infusion device 100 illustrated in FIGS. 1-4 also includes a pressure sensor 144 that is connected to the passageway 120 between the outlet of the fluid transfer device 114 and the outlet port 118. As such, the pressure sensor 144 senses the pressure at the outlet port 118 which, in the illustrated embodiment, is also the pressure within the catheter 122. The pressure sensor 144 is connected to the controller 136 and may be used to analyze a variety of aspects of the operation of the exemplary implantable infusion device 100. For example, pressure measurements may be used by the controller 136 to determine whether or not there is a blockage in the catheter 122, as is described below with reference to FIGS. 7 and 8, and whether or not the fluid transfer device 114 is functioning properly. The controller 136 may perform a variety of different functions in response to a determination that the fluid transfer device 114 is not functioning properly or a determination that the catheter 122 is blocked. For example, the controller 136 may actuate an audible alarm 148 that is located within the housing 102 in order to signal that the fluid transfer device 114 is not functioning properly or the catheter 122 is blocked.

Turning to FIGS. 5 and 6, the exemplary implantable infusion device 100 may be included in an infusion device system 10 that also includes a remote control 200 that is not implanted in the patient. The exemplary remote control 200 includes a housing 202, a touch screen display 204 (or other input device, such as a keypad, with or without a separate display), a battery or other power source 206, a controller 208, such as a microprocessor, microcontroller or other control circuitry, memory 210, and a communication device 212 (including an antenna if necessary). Although the present inventions are not limited to any particular communication device, the exemplary communication device 212 is a telemetry device that transmits an RF signal at a specified frequency. The RF signal may, in some instances, be a carrier signal that carries bit streams. The communication device 212 is configured to send signals to and receive signals from the communication device 132 in the implantable infusion device 100 by way of the antenna 134. Other exemplary communication devices include oscillating magnetic field communication devices, static magnetic field communication devices, optical communication devices, ultrasound communication devices and direct electrical communication devices. In some instances, the remote control may also include an audible alarm 214.

The exemplary remote control 200 may be used to perform a variety of conventional control functions including, but not limited to, turning the infusion device ON or OFF and programming various infusion device parameters. Examples of such parameters include, but are not limited to, the rate of delivery of a given medication, the time at which delivery of a medication is to commence, and the time at which delivery of a medication is to end. Additionally, in at least some implementations, the implantable infusion device 100 will transmit signals to the remote control 200. The signals provide status information about the infusion device 100 that may be stored in memory 210 and/or displayed on the display 204.

Examples of such status information include, but are not limited to, the state of charge of the battery 126, the amount of medication remaining in the reservoir 110, the amount of medication that has been delivered during a specified time period, and the presence of a catheter blockage. The signals from the infusion device 100 may also be indicative of sensed physiological parameters in those instances where the infusion device is provided with physiological sensors (not shown).

As alluded to above, catheter pressure measured by the pressure sensor 144 may be used by the controller 136 to determine whether or not the catheter 122 is blocked because pressure within the catheter will increase as a result of the blockage. When the catheter 122 is partially blocked, the amount of fluid that passes through the outlet 124 after each stroke will be less than what is supplied to the catheter by the fluid transfer device 114 during the stroke. The pressure within the catheter 122 will, therefore, increase (or "accumulate") after each stroke. Pressure will also accumulate, albeit more rapidly, when the catheter is completely blocked. Increases in sensed pressure may, however, be due to factors other than a compete or partial blockage of the catheter 122. Most notably, changes in environmental pressure, which may be the result of changes in altitude or the weather, will also be sensed by the pressure sensor 144.

In order to reduce the likelihood that changes in environmental pressure will result in false blockage determinations, and as illustrated in FIG. 7, the pressure measured by the sensor 144 (Step 01) may be analyzed by the controller 136 in the context of other factors associated with the fluid transfer process (Step 02). Such factors, which include the amount of time that passes and/or the number of fluid transfer device operations (e.g. pump strokes) and/or the volume of fluid transferred to the catheter, may be used to determine that certain increases in catheter pressure could not have been due to the fluid transfer device transferring fluid into a blocked catheter. For example, the controller 136 may determine whether or not there is a blockage based on (1) the total sensed pressure change over the course of a relatively long time window ("$\Delta P_{window}$") and (2) the sensed pressure changes during relatively short periods that together make up the relatively long time window ("$\Delta P_{1, 2, \ldots n}$"). The total sensed pressure change $\Delta P_{window}$ may be used to determine whether or not there has been a pressure increase that is large enough to have been the result of a blockage over the entire time window. The periodic pressure changes $\Delta P_{1, 2, \ldots n}$ may be used to identify changes in catheter pressure that occur within the time window and are due to changes in environmental pressure. For example, in some implementations, the controller 136 will not make a blockage determination if one or more of the periodic pressure changes $\Delta P_{1, 2, \ldots n}$ is too large to be the result of a blockage despite the fact that the total sensed pressure change $\Delta P_{window}$ is large enough to be the result of a blockage. A periodic pressure change $\Delta P_{1, 2, \ldots n}$ that is too large to be the result of a blockage could, for example, be the result of the user going scuba diving and quickly descending.

Figure 8:
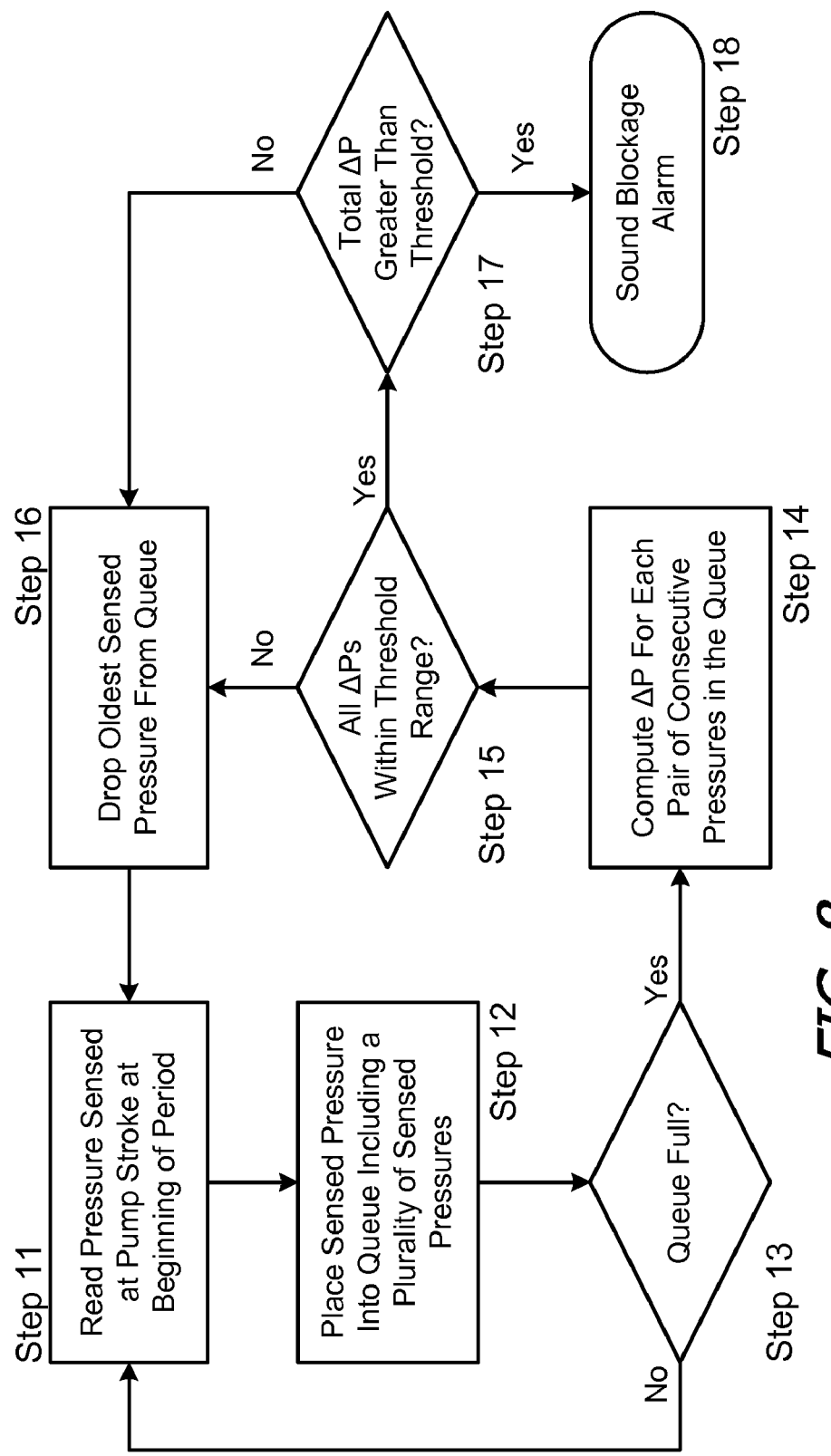
FIG. 8 is a flow chart in accordance with one embodiment of a present invention.

FIG. 8 is an illustration of one example of a process in which a plurality of pressure measurements are taken during a sliding time window, and then compared to pressures measurements that would be expected if the catheter were, in fact, blocked. In the illustrated example, the pressure measured by the pressure sensor 144 is read every half-hour during a four hour sliding time window by the controller 136, with the first reading taken at the beginning of the four hour time window (Step 11). The pressure sensor readings occur either before or after the fluid transfer device operation (e.g. pump stroke). Each of the measured pressures are stored by the controller 136 in a queue in the order in which they were read (Step 12). The reading/storage process will continue until the queue is full (Step 13). In the illustrated example, the queue will include nine (9) sensed pressures, i.e. the pressure sensed at the beginning of the four hour window and the pressures sensed every half-hour thereafter until the end of the four hour window. Thus, the initial sensed pressures stored in the queue will be $P_0, P_1 \ldots P_8$.

Once the queue is full, the controller 136 will calculate the pressure change $\Delta P_{1, 2, \ldots n}$ associated with each pair of consecutive pressure sensor readings (Step 14) and, therefore, the periodic pressure change associated with each half-hour period. In the illustrated example, there will be eight (8) periodic pressure changes associated with pressures sensed within the sliding time window queue, i.e. $\Delta P_1 = P_1 - P_0$, $\Delta P_2 = P_2 - P_1 \ldots \Delta P_8 = P_8 - P_7$. The controller 136 will then determine whether or not each of the periodic pressure changes $\Delta P_{1-8}$ is within a predetermined threshold range of pressure changes (Step 15). The threshold range is a range of pressure changes that would be expected if the fluid transfer device was transferring fluid into a blocked catheter for the associated period (here, a half-hour). The threshold range may also take into account small atmospheric (or "barometric") pressure decreases that may occur during each period due to typical changes in the weather (e.g. −0.5 psi). Typical changes in the weather would exclude changes in the barometric pressure associated with hurricanes, tornados and the like. The threshold range of pressure changes may, for example, be between a pressure change that is slightly less than the expected pressure increase (including pressure decreases that may result from a decrease in atmospheric pressure during the period that is greater in magnitude than the pressure increase associated with a blockage) and a pressure change that is slightly greater than the expected pressure increase. Accordingly, Step 15 in the exemplary implementation insures that (1) there are consistent blockage-based additions to catheter pressure over the entire time window, i.e. that the pressure changes $\Delta P_{1-8}$ are all greater than zero or, when there is a decrease, the decrease is less than the largest decrease that could be associated with a weather-related change in atmospheric pressure, and (2) that no periodic increase (e.g. pressure change $\Delta P_4$) is due to environmental factors other than typical weather. The low and high ends of the threshold range may be increased and/or decreased as desired in order to increase or decrease the likelihood that there will be a blockage detection, as is discussed below.

If any of the calculated pressure changes $\Delta P_{1-8}$ are outside the threshold range, i.e. are less than the low end of the threshold range or are greater than the high end of the threshold range, it is assumed that there is no blockage. The monitoring and analysis will, however, continue. More specifically, the sliding time window will slide forward one period (here, one half-hour) in first-in first-out fashion. This is accomplished by dropping the oldest sensed pressure from the queue (Step 16), adding the pressure that is measured at the beginning of the next period to the queue (Steps 11 and 12), and again determining whether any of the periodic pressure changes $\Delta P_{1-8}$ are outside the threshold range. This will continue so long as there is at least one periodic pressure change $\Delta P_{1, 2, \ldots n}$ in the queue that is outside the threshold range.

If, on the other hand, all of the periodic pressure changes $\Delta P_{1-8}$ are within the threshold range, the controller 136 will determine whether or not the total pressure change $\Delta P_{window}$ that occurred over the entire time window, i.e. the sum of the periodic pressure changes $\Delta P_{1-8}$, is greater than a predetermined threshold (Step 17). The threshold pressure change is indicative of the change in pressure that would be expected if the fluid transfer device was transferring fluid into a blocked catheter for an entire time window (here, four hours). This value may be increased and/or decreased as desired in order to increase or decrease the likelihood that there will be a blockage detection, as is discussed below. The controller 136 may perform a variety of different functions if the total pressure change $\Delta P_{window}$ is greater than the threshold. For example, the controller 136 may actuate the audible alarm 148 that is located within the housing 102 in order to alert the person in which the infusion device 100 is implanted (Step 18). An audible alarm may also be used to advise the person that the blockage is no longer present. This may occur, for example, when the blockage is due to a kink caused by movement and unkinking cause by subsequent movement. The controller 136 may cause the communication device 132 to transmit information about the blockage to an external device such as remote control 200, which may in turn provide audible or visual information about the blockage, or to a clinician's programming unit. Information about the blockage may also be stored in memory within the infusion device 100 so that it may be accessed later.

Alternatively, if the total pressure change $\Delta P_{window}$ is less than the threshold, it is assumed that there is no blockage. The monitoring will, however, continue. More specifically, the sliding time window will slide forward one period (here, one half-hour) by dropping the oldest sensed pressure from the queue (Step 16), and adding the pressure that is measured at the beginning of the next period to the queue (Steps 11 and 12). The analysis of the sensed pressure will then proceed in the manner described above.

In the exemplary process described above with respect to FIG. 8, the controller 136 performs a time-based analysis of pressure measurements. Alternatively, or in addition, the pressure measurements may be analyzed in the context of fluid transfer device operations. More specifically, instead of defining the sliding measurement window and/or the periods within the sliding measurement window in the time domain (e.g. hours and portions thereof), the pressure measurements may be analyzed in the context of pump strokes or other fluid transfer device operations (e.g. rotor actuation and/or incremental angular advancement in a peristaltic pump) that result in fluid being transferred to a catheter. Each period may be a predetermined number of pump strokes and the sliding window may be a predetermined number of periods. For example, if one wanted to achieve the same results as the half-hour/four hour analysis described above and the fluid transfer device averaged 1 operation (e.g. pump stroke) per minute, each period would consist of 30 pump strokes and the sliding window would consist of 240 pump strokes. Windows may also be based on delivery volume, energy consumption and other factors.

The exemplary process described above with respect to FIG. 8 may also be modified, without changing the ultimate result, by reversing the position of Step 15 and Step 17.

It should be noted that the pressure increases associated with blockages are a function of the catheter construction, i.e. its internal volume and compliance, and amount of fluid that has been driven into the blocked catheter. Such pressure increases may be calculated or experimentally determined and stored in a look-up table on a catheter-by-catheter basis. The look-up table may be stored in memory 138 and used by the controller to perform the analysis described above. The catheter will be identified when the fluid transfer device 100 is installed and/or programmed.

It should also be noted that the desire to avoid false blockage determinations must be weighed against the desire to promptly alert the user that there is a blockage. Accordingly, various aspects of the process described above with respect to FIG. 8 may be modified. For example, the amount of time (or number of fluid transfer device operations) associated with the sliding time window, as well as the magnitude of the threshold total pressure change $\Delta P_{window}$, may be decreased in order to provide a more rapid blockage determination. This would increase the likelihood of false positives by making it more likely that environmental factors will trigger a blockage determination. Additionally, the threshold range of the periodic pressure changes $\Delta P_{1-8}$ may increased by decreasing the low end of the range and/or increasing the high end of the range. For example, the threshold range may extend from slightly less (i.e. 10% to 20% less) than a weather-related pressure drop to a pressure that is slightly greater (i.e. 10% to 20% greater) than the sum of the expected pressure increase and a weather-related pressure increase (e.g. about −0.6 psi to about 3.5 psi). Such an increase in range increases the likelihood that a blockage determination will be made.

Although the inventions disclosed herein have been described in terms of the preferred embodiments above, numerous modifications and/or additions to the above-described preferred embodiments would be readily apparent to one skilled in the art. By way of example, but not limitation, the present inventions have application in infusion devices that include multiple reservoirs and/or outlets. It is intended that the scope of the present inventions extend to all such modifications and/or additions and that the scope of the present inventions is limited solely by the claims set forth below.

We claim:

1. A method of operating an infusion device including a fluid transfer device and a catheter, the method comprising the steps of:
    transferring fluid to the catheter with the fluid transfer device a plurality of times during a measurement window;
    sensing catheter pressure a plurality of times during the measurement window;
    storing a plurality of sensed pressures in a queue in the order that the pressures were sensed;
    computing the pressure differences between time adjacent pairs of sensed pressures; and
    determining whether an increase in sensed pressure during the measurement window corresponds to an increase in sensed pressure that would result from a catheter blockage.

2. A method as claimed in claim 1, wherein the sensing step comprises sensing catheter pressure immediately after a transfer by the fluid transfer device.

3. A method as claimed in claim 1, wherein the determining step comprises:
    determining whether each of the pressure differences is within a predetermined range; and
    determining whether the sum of the pressure differences is greater than a predetermined sum threshold.

4. A method as claimed in claim 3, wherein the predetermined range is between the largest decrease that would be associated with the weather and a value that is slightly larger than the pressure increase that would result from a blockage.

5. A method as claimed in claim 1, wherein the measurement window is a first-in first-out measurement window, the method further comprising the step of:
    deleting the oldest sensed pressure from the queue after the queue becomes full.

6. A method of operating an infusion device including a fluid transfer device and a catheter, the method comprising the steps of:
   transferring fluid to the catheter with the fluid transfer device a plurality of times during a measurement window of a plurality of hours;
   sensing catheter pressure a plurality of times during the measurement window;
   storing a plurality of sensed pressures in a queue in the order that the pressures were sensed;
   computing the pressure differences between time adjacent pairs of sensed pressures; and
   determining whether there are consistent blockage-based additions to catheter pressure during the measurement window that correspond to a catheter blockage.

7. A method of operating an infusion device including a fluid transfer device and an outlet, the method comprising the step of:
   signaling that a blockage has been detected in response to consistent blockage-based additions to outlet pressure that are within a predetermined range and persist over a plurality of hours.

8. A method as claimed in claim 7, wherein the predetermined range is between the largest decrease that would be associated with the weather and a value that is slightly larger than the pressure increase that would result from a blockage.

9. A method as claimed in claim 7, wherein the predetermined range is between the largest decrease that would be associated with the weather and a value that is 10% to 20% greater than the pressure increase that would result from a blockage.

10. An infusion device for use with a catheter, comprising:
    an outlet port configured to be secured to the catheter;
    a fluid transfer device operably connected to the outlet port;
    a pressure sensor located between the fluid transfer device and the outlet port; and
    a controller that differentiates between increases in sensed pressure that are the result of changes in environmental pressure and increases in sensed pressure that are the result of a catheter blockage by calculating a plurality of individual pressure differences, calculating the sum of the plurality of individual pressure differences only if each of the pressure differences is within a predetermined range, and comparing the sum to a predetermined sum threshold.

11. An infusion device as claimed in claim 10, wherein the fluid transfer device comprises an electromagnet pump.

12. An infusion device as claimed in claim 10, wherein the controller is configured to determine whether a plurality of pressures sensed periodically throughout a predetermined measurement window correspond to consistent blockage-based additions to pressure.

13. An infusion device for use with a catheter, comprising:
    an outlet port configured to be secured to the catheter;
    a fluid transfer device operably connected to the outlet port;
    a pressure sensor located between the fluid transfer device and the outlet port; and
    a controller configured to
    store a plurality of sensed pressures in a queue,
    compute the pressure differences between time adjacent pairs of sensed pressures in the queue,
    determine whether each of the pressure differences is within a predetermined range, and
    determine whether the sum of the pressure differences is greater than a predetermined sum threshold.

14. An infusion device as claimed in claim 13, wherein the predetermined range is between the largest decrease that would be associated with the weather and a value that is slightly larger than the pressure increase that would result from a blockage.

15. An infusion device as claimed in claim 13, wherein the predetermined range is between the largest decrease that would be associated with the weather and a value that is 10% to 20% greater than the pressure increase that would result from a blockage.

16. An infusion device as claimed in claim 13, wherein the controller is further configured to
    delete the oldest sensed pressure from the queue after the queue is full.

17. An infusion device for use with a catheter, comprising:
    an outlet port configured to be secured to the catheter;
    a fluid transfer device operably connected to the outlet port;
    a pressure sensor located between the fluid transfer device and the outlet port; and
    means for storing a plurality of pressures sensed during a measurement window; and
    means for calculating a plurality of individual pressure differences between pairs of sensed pressures, calculating the sum of the plurality of individual pressure differences only if each of the pressure differences is within a predetermined range, and comparing the sum to a predetermined sum threshold to determine whether an increase in sensed pressure during the measurement window corresponds to an increase in sensed pressure that would result from a catheter blockage.

18. An infusion device as claimed in claim 17, wherein the fluid transfer device comprises an electromagnet pump.

19. A method as claimed in claim 7, wherein
    the fluid transfer device comprises a pump; and
    the consistent blockage-based additions to outlet pressure that are within a predetermined range comprises blockage-based additions to outlet pressure within the predetermined range that occur after each pump stroke.

20. An infusion device as claimed in claim 10, wherein the changes in environmental pressure comprise changes in altitude.

21. An infusion device as claimed in claim 10, wherein the changes in environmental pressure comprise changes in weather.

22. A method as claimed in claim 6, wherein the sensing step comprises sensing catheter pressure immediately after a transfer by the fluid transfer device.

23. A method as claimed in claim 6, wherein the measurement window is a first-in first-out measurement window, the method further comprising the step of:
    deleting the oldest sensed pressure from the queue after the queue becomes full.

* * * * *